United States Patent [19]

Soule et al.

[11] Patent Number: 5,436,152
[45] Date of Patent: * Jul. 25, 1995

[54] IMMORTAL HUMAN MAMMARY EPITHELIAL CELL LINES

[76] Inventors: Herbert Soule, 6344 Jonathan, Dearborn, Mich. 48126; Charles M. McGrath, 6669 Beach, Troy, Mich. 48098

[*] Notice: The portion of the term of this patent subsequent to Jun. 25, 2008 has been disclaimed.

[21] Appl. No.: 702,808

[22] Filed: May 20, 1991
(Under 37 CFR 1.47)

Related U.S. Application Data

[63] Continuation of Ser. No. 317,610, Feb. 28, 1989, Pat. No. 5,026,637.

[51] Int. Cl.⁶ .......................... C12N 5/00; C12N 5/08
[52] U.S. Cl. .................. 435/240.2; 435/240.1
[58] Field of Search ............... 435/240.1, 240.2

[56] References Cited

U.S. PATENT DOCUMENTS

| | | | |
|---|---|---|---|
| 4,423,145 | 12/1983 | Stampfer et al. | 435/240 |
| 4,808,532 | 2/1989 | Stampfer | 435/240.2 |
| 5,026,637 | 6/1991 | Soule et al. | 435/240.1 |

OTHER PUBLICATIONS

In Vitro, vol. 20, No. 8 Aug. 1984, "Calcium Regulation of Normal Human Mammary Epithelial Cell Growth In Culture," Charles M. McGrath and Herbert D. Soule, pp. 635–662.

In Vitro Cellular & Developmental Biology, vol. 33, No. 1, Jan., 1986, "A Simplified Method For Passage And Long-Term Growth of Human Mammary Epithelial Cells," Herbert D. Soule and Charles M. McGrath, pp. 6–12.

Jones et al., Proceedings of AACR vol. 29 Mar. 1988, #1780, p. 448.

*Primary Examiner*—Douglas W. Robinson
*Assistant Examiner*—Susan M. Weber
*Attorney, Agent, or Firm*—Dykema Gossett

[57] ABSTRACT

Immortalized human epithelial cell sublines are provided. The novel cell lines do not undergo terminal differentiation and senescence upon exposure to high calcium concentrations. The novel cells exhibit positive reactivity with milk-fat globule membrane antigen and cytokeratin anti-serum. The cells are non-tumorigenic in athymic mice, and exhibit both three-dimensional growth in collagen and dome formation in confluent cultures. The cell sublines demonstrate growth control by hormones and growth factors. The novel cell sublines are useful in evaluating the capacity of preselected agents to bring about a change in epithelial cell growth and in the production of proteins.

4 Claims, 3 Drawing Sheets

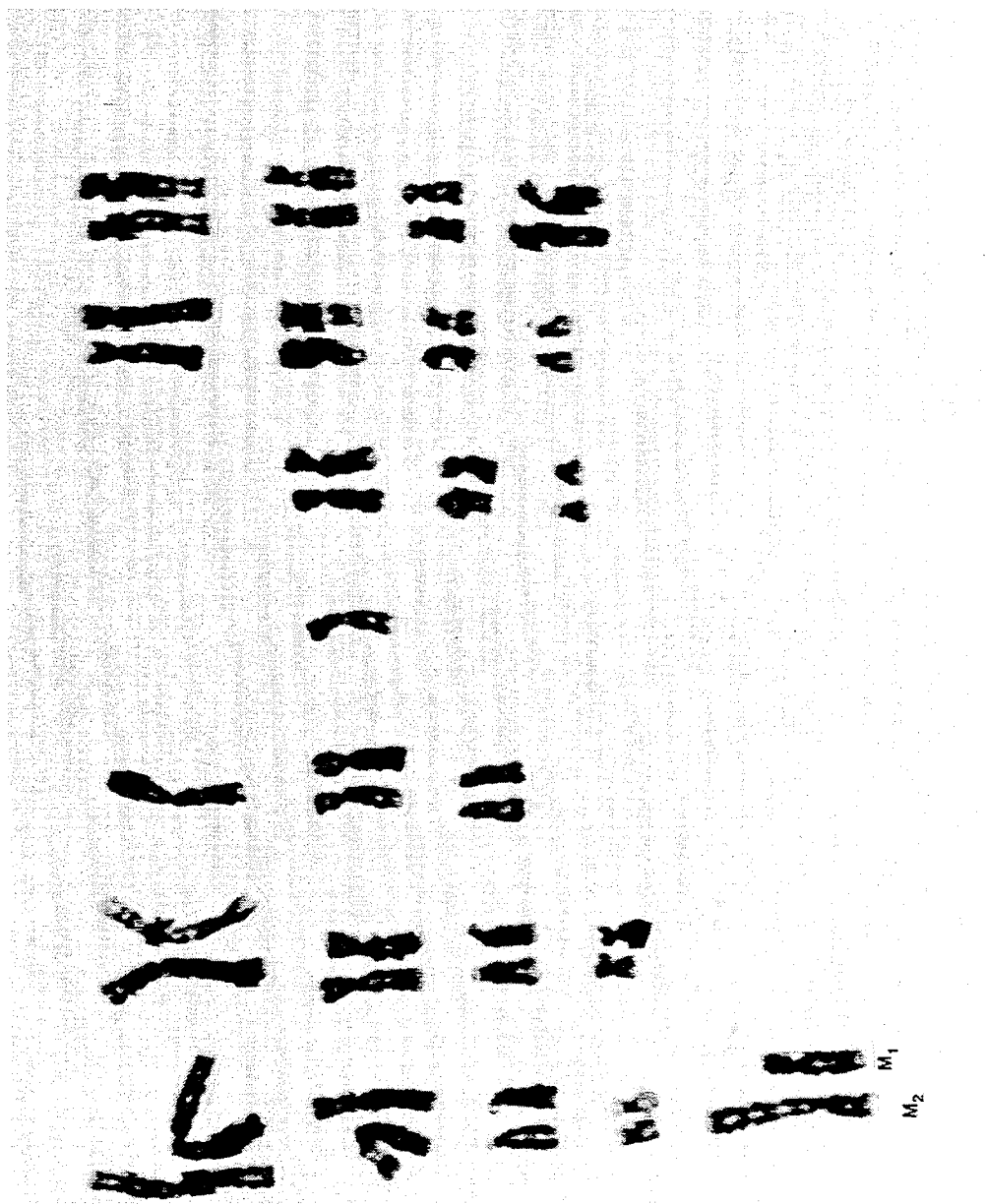

IMMORTAL HUMAN MAMMARY EPITHELIAL CELL LINES

This is a continuation of application Ser. No. 07/317,610 filed on Feb. 28, 1989 now U.S. Pat. No. 5,026,637.

The discovery of the present invention was supported by PHS Grant CA38921, CA36399 and CA18175 and an institutional grant from the United Foundation.

FIELD OF THE INVENTION

The present invention relates generally to human epithelial cells. More specifically, the present invention provides an immortalized human mammary epithelial cell line and methods of using the novel cells in research and industry.

BACKGROUND OF THE INVENTION

The principle of limited cell division potential of somatic cells *in vitro* as demonstrated by Hayflick and others is well established. In order to overcome this limitation, somatic cell hybridization is routinely used to produce immortalized cell lines for the production of proteins. As will be appreciated by those skilled in the art, somatic cell hybridization involves the fusion of a somatic cell having limited division potential with an immortal tumor cell to produce an immortal hybridoma. In this manner, a continuous cell line can be established from which the desired protein is collected.

In a number of fields, researchers utilize somatic cell cultures derived from normal tissues in order to study the mechanisms underlying intercellular interaction and cellular response to various stimuli. These include such diverse pursuits as evaluating the carcinogenicity of selected agents, determining the activities of various hormones, monitoring the reactions of chemotherapeutic agents, and in general studying the metabolic characteristics of a given cell type. However, the phenomenon of limited cell division of normal cells complicates these efforts and often prevents long-term evaluation of cell sensitivity and induced expression.

More specifically, the study by oncologists of neoplastic transformation of epithelial cells has been severely limited by the relatively limited *in vitro* population longevity. This has led to the use of human fibroblast cultures which have greater *in vitro* longevity as the accepted model for transformation studies. However, it has been noted that the analogy drawn between these two distinct cell-types is tenuous at best and that the lack of a true long-term epithelial model has hindered cancer research. This is despite the fact that neoplasms of epithelial origin are the most prevalent type of cancer in humans.

In particular, it is known that conventional human mammary epithelial cells have at most a limited cell division potential of from about 30 to 64 doublings. As disclosed in "A Simplified Method For Passage and Long-Term Growth of Human Mammary Epithelial Cells," *In Vitro Cellular and Developmental Biology*, Vol 22, No. 1, January, 1986, which is incorporated herein by reference, the inventors of the present invention discovered a method of culturing non-neoplastic human mammary epithelial cells which extends the population longevity of these cells beyond the previously reported limit of 13 doublings to more than 50 generations. Although Hammond and coworkers have reported that doublings in excess of 13 can be achieved by supplementing the culture media with bovine pituitary extract, this method required multiple enzymatic transfers and requires high ionic calcium ($Ca^{++}$) concentrations. In the aforementioned work of the present inventors, longevity was achieved by reducing the $Ca^{++}$ concentration of the media which in turn reduced an inhibition effect in which glucocorticoides induced terminal differentiation. A significant observation which was made in these studies was that conventional human mammary epithelial cells in culture media greater than 0.06 mM ionic calcium underwent terminal differentiation after only three or four divisions in primary culture. It is believed that there may exist epithelial cell lines developed by others which have extended division potential, although they are not the cell lines of the present invention.

It would therefore be desirable to provide a non-neoplastic epithelial cell line which could be cultured indefinitely to permit long-term evaluation of suspected reactive agents. It would also be desirable to provide such a cell line which produces a normal complement of proteins characteristic of normal epithelial cells. It would be further desirable to provide a method by which epithelial cell sensitivity to suspected reactive agents and cellular expression thereby induced could be studied on a long-term basis. The present invention satisfies these goals by providing non-neoplastic human mammary epithelial cells for use in cell culture studies.

SUMMARY OF THE INVENTION

In accordance with the present invention there is provided in one aspect two sublines of one immortal non-neoplastic human mammary cell line, the sublines being designated MCF-10A and MCF-10F which have unlimited cell division potential and which produces a normal complement of mammary epithelial cell proteins. The novel cell sublines of the present invention are provided as a biologically pure cultures and are capable of subsisting in a high-calcium media without undergoing calcium-induced cellular senescence. MCF-10A and MCF-10F are non-tumorigenic in athymic mice and demonstrates a characteristic response to treatment with insulin, epidermal growth factor and cortisol.

In still another aspect, the present invention provides a method for testing the long-term biological activity of a preselected agent on epithelial cell growth *in vitro* which comprises the steps of exposing a culture of immortalized human mammary epithelial cells, as provided by the present invention under the designation MCF-10A or MCF-10F, to a preselected agent and monitoring cellular sensiti and/or induced altered cellular expression.

In still another embodiment of the present invention, a method for the production of proteins, preferably in continuous culture, is provided comprising the steps of culturing the novel human mammary epithelial cell line MCF-10A or MCF-10F of the present invention and collecting one or more proteins produced by the novel cells.

Hence, it is an object of the present invention to provide two immortal sublines of a non-neoplastic human mammary epithelial cell line to be used as a model in epithelial cell studies.

It is a further object of the present invention to provide a method by which the activities of preselected agents on epithelial cells can be observed over extended periods.

Yet another object of the present invention is to provide an immortal non-neoplastic human epithelial cell line which can be utilized in a method of producing a preselected protein and a method of producing proteins of epithelial cell origin.

These and other objects and advantages of the present invention will become apparent through the following description of the preferred embodiments of the invention and with reference to the drawings in which:

BRIEF DESCRIPTION OF THE DRAWINGS

FIG. 3 is a karyotype of MCF-10A propagated as trypsin-versene passages grown in high-calcium medium.

DESCRIPTION OF THE PREFERRED EMBODIMENTS

Figure 1:
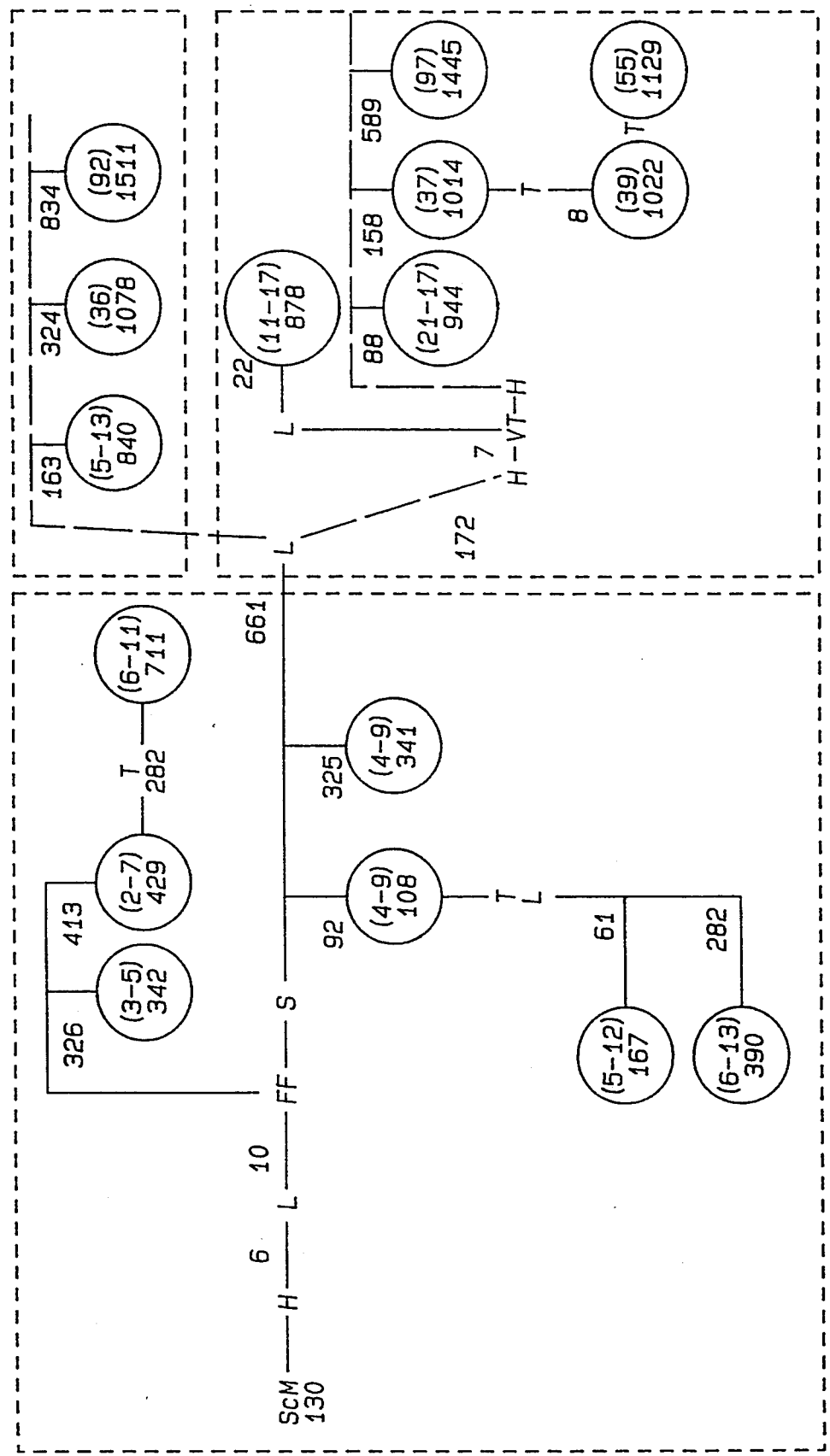
FIGS. 1A, 1B and 1C are a flowchart illustrating the origin of the novel epithelial cell line of the present invention.

The present invention provides two sublines of a non-neoplastic immortal human epithelial cell line designated herein as MCF-10A and MCF-10F, respectively. Cultures of MCF-10A and MCF-10F have been deposited with the American Type Culture Collection in Rockville, Maryland and have be assigned ATCC Registration No. CRL 10317 for MCF-10A and ATCC Registration No. CRL 10318 for MCF-10F. The deposit(ry has been instructed to afford permanence of the deposits for at least thirty years or at least five years after the most recent storage request, whichever is longest. Should the deposited cells become non-viable or be inadvertently destroyed, the cultures will be replaced for at least thirty years from the date of the original deposit or at least five years from the date of the most recent request for release of a sample or for the life of any patent issued on this application, whichever period is longer. With respect to the availability of the cultures, the aforementioned deposits will be made under conditions which assure ready accessibility to the cultures by the public if a patent is granted on this application, whereby all restrictions to the availability to the public of the deposited culture will be irrevocably removed upon granting of the patent. Access to the cultures will be available during the pendency of the patent application to one determined by the Commissioner of Patent and Trademarks to be entitled thereto.

The immortal cell line of the present invention comprises human mammary epithelial cells which are cytogenetically normal. MCF-10A and MCF-10F express cytokeratins, milk-fat globule antigens and other conventional mammary epithelial markers. The novel cell sublines of the present invention are resistant to high-calcium induced senescence which is typical of most prior art human mammary epithelial cells. MCF-10A and MCF-10F are further characterized by unlimited (immortal) cell division potential. MCF-10A and MCF-10F are growth-responsive to insulin and/or epidermal growth factor, cholera enterotoxin, and cortisol. MCF-10A and MCF-10F are non-tumorigenic in athymic mice. The novel cell sublines of the present invention also demonstrate three-dimensional growth in collagen, dome formation in confluent cultures and anchorage dependent growth characteristic of normal human mammary epithelial cells. Applicants believe that MCF-10A and MCF-10F are immortal without substantial alteration of the characteristics of normal human breast epithelium and its conventional phenotypes.

MCF-10A and MCF-10F were produced by in vitro mutation. A causative, i.e. mutagenic, agent has not been identified, and thus the mutation shall be referred to herein as "spontaneous." In order to more fully understand the Applicants' novel cell line, the protocol which was utilized in discovery of the present invention will now be fully explained.

Tissue samples were obtained from subcutaneous mastectomies. To process the tissue for culture, the samples were sliced to diameters of 0.5 cm (Stadie-Riggs microtome) and observed microscopically to determine the presence of normally dense stroma and parenchyma. The samples were then minced to fragments using a scalpel. These fragments were then further divided into cells and cell aggregates or organoids by treatment with collagenase and hyaluroniadase using the procedures set forth in "Growth of Normal Human Mammary Cells In Culture," *In Vitro*, 615:415–425 (1980) which is incorporated herein by reference. Ten micrograms/ml insulin and 1.4 $\mu$M cortisol were included, with 10% serum in the digestion mixtures as detailed in "Calcium Regulation Normal Human Mammary Epithelial Cell Growth in Vitro: Cortisol and the Recruitment Cells to Terminal Differentiation," *J. Cell Physiol.*, 116:38514 396 (1983) which is incorporated herein by reference.

The resultant disassociated epithelium was then plated in primary culture as fully described in the immediately foregoing reference. Cell number was estimated from packed cell volumes. 75 cm$^2$ flasks were generally used for the primary cultures. Succeeding cultures were plated in T-25 flasks, T-75 flasks or 24-well plates. Attached cells were subcultivated using 0.05 trypsin and 0.025% versene in a balanced salt solution free of Ca$^{++}$ and Mg$^{++}$ or by passing free-floating cells. Cell viability was determined by the trypan blue exclusion test using a hemocytometer. Cell number and viability of the seed flasks were determined by performing a cell count when the nutrients were replenished. The number of doublings that occurred during the extended time periods in culture was calculated by determining total cell number released from a constant cell number that remained attached in confluent cultures or by counting cells plated or attached on day one post transfer and cell number at transfer.

The culture media employed in these studies will now be generally described. A 1:1 ratio of Dulbecco and Ham's F12 nutrients in admixture was utilized. The medium was prepared *de novo* from the constituent compounds, using vitamins and amino acids obtained from Sigma Chemical Company. A basal salt solution was prepared without CaCl$_2$. Nutrients and salts were adjusted to a pH of 7.2 using HCl and NaOH and sterilized by filtration with 0.22 micrometer filters. Sterile CaCl$_2$ was added from 500 or 28.5 mM stocks to obtain 1.05 or 0.04 mM Ca$^{++}$, respectively. Divalent cations were removed from serum using Chelex 100, sodium form, obtained from Bio-Rad Laboratories pursuant to the method set forth in "Improved Methods for Reducing Calcium and Magnesium Concentration in Tissue Culture Medium: Application to Studies of Lymphoblast Proliferation In Vitro," *In Vitro*, 11:354–360 (1975), which is incorporated herein by reference. The level of calcium in the solutions was monitored by flame photometry. The serum was sterilized by filtration with 0.45 micrometer filters and was then maintained at -20°

C until use. 100 U/ml penicillin, 100 micrograms/ml streptomycin, amphotericin B 2.5 micrograms/ml, 100 ng/ml cholera enterotoxin and 20 ng/ml epidermal growth factor were used to supplement the media, as was 5% horse serum. 10 micrograms/ml insulin and $1.4 \times 10^{-6}$M cortisol were also routinely included in the media.

During these experiments, Applicants were able to significantly extend the population longevity of epithelial cells without the continuous use of high calcium concentrations or enzymatic transfers as is more fully disclosed in "A Simplified Method For Passage and Long-Term Growth of Human Mammary Epithelial Cells," *In Vitro*, Vol. 22, No. 1 (January 1986) which is incorporated herein by reference. By continuing these cultures, Applicants produced the two immortalized epithelial cell sublines MCF-10A and MCF-10F of the present invention. One of the human mammary epithelial cell samples which had been prepared in the aforementioned manner by first culturing the cells in complete medium with a high (1.05 mM) $Ca^{++}$ concentration and then changing to complete medium with a low (0.04–0.06 mM) $Ca^{++}$ concentration produced free-floating cells which were subsequently found to have mutated to an immortal non-neoplastic state. More specifically, after 843 days in 0.03–0.06 mM $Ca^{++}$ (661 days serum-free but with 1 mg fetuin and 5 micrograms of transferrin per ml), the culture was split. MCF-10F was maintained by free-floating passages with 0.04 mM $Ca^{++}$, and MCF-10A was transferred serially with trypsin-versene in 1.05 mM $Ca^{++}$ with 5% equine serum. These cells are characterized by continued growth in high-calcium medium which was not inherent in the original tissue from which MCF-10A and MCF-10F were derived or of cryopreserved cells of these cultures which were prepared at 0.3 and 1.2 years in low calcium. The mutation occurred sometime after 667 days in culture.

As used herein, the term "immortal" or "immortalized" shall mean that, based upon current observations, these cells, under the culture conditions described herein have shown no tendency to undergo terminal differentiation and cell senescence, but rather retain the capacity to divide indefinitely. By "non-neoplastic," it is meant that the novel cell lines of the present invention demonstrate no indicia characteristic of neoplastic cells other than immortality and are non-tumorigenic when injected in athymic mice.

The preferred culture medium for MCF-10F is Dulbecco and Ham's F-12 (1:1 ratio) 95%, 5% equine serum, epidermal growth factor 20 ng/ml, bovine insulin 10 pg/ml, cholera enterotoxin and cortisol 1.4 $\mu$M, penicillin 100 units/ml, streptomycin 100 $\mu$g/ml, and amphotericin B 0.25 $\mu$g/ml with divalent ions removed from equine serum with Chelax 100 and Dulbecco and Ham's F-12 prepared without $CaCl_2$ and $Ca^{++}$ added to obtain 0.04 mM concentration. The preferred culture medium for MCF-10A is prepared in the same manner as MCF-10F except the divalent ions are not removed from the equine serum. The Dulbecco and Ham's F-12 are prepared with $Ca^{++}$ to obtain a 1.05 mM concentration. MCF-10A is preferably grown as monolayers, transferred 1:25 weekly. MCF-10F is preferably grown as monolayers which yield free-floating cells and are transferred 1:4 weekly with free-floating cells. MCF-10A and MCF-10F have been maintained in vitro with full cell division potential in excess of four years.

To more fully describe the present invention, Table I below sets forth the protocol used to prepare the media used in the initial cultures of the tissue sample which gave rise to MCF-10A and MCF-10F.

TABLE I

F = 12 + Dulbecco's No $Ca^{++}$ 20 liters
DISSOLVE COMPONENTS IN VOLUME
INDICATED AND COMBINE IN FOLLOWING ORDER

|    |   |   | #of additives | Total Volume |
|----|---|---|---|---|
| 1. | amino acids | 2500 ml $H_2O$ | ... 1–19 | 2500 ml |
| 2. | 6N HCl | 20 ml (on magnetic stirrer until completely dissolved; read pH) | | 2520 |
| 3. | 6N NaOh | ~22 ml KEEP RECORD OF VOLUME to bring pH to 7.0 | | 2542 |

THE AMOUNT OF Na AND Cl ADDED TO SOLUBILIZE THE AMINO ACIDS MUST BE DETERMINED AND THEN SUBTRACTED FROM THE TOTAL NaCl TO BE ADDED.

6N NaOH = .24 gms/ml .24 × 22 = 5.28 gms NaOH
5.28 × .575 (Na/NaOH) = 3.04 gms added as Na
3.04 × 1.54 (Cl/Na) = 4.68 gms added as Cl
3.04 + 4.68 = 7.72 gms of Na, Cl added
139990 − 7720 = 1332270 mg NaCl to be added

|    |   |   |   |   |
|----|---|---|---|---|
| 4. | $H_2O$ | 458 ml (VARY AS TO NaOH ADDED | | 3000 |
| 5. | tryptophane | 300 ml | 20 | 3000 |
| 6. | sodium pyruvate | 300 ml | .22 | 3300 |
| d7. | vitamins | 500 ml | 23–29 | 4100 |
| 8. | riboflaven | 100 ml | 30 | 4200 |
| 9. | rinse $H_2O$ | 1000 ml | | 5200 |
| 10 | B12, putrescine | 100 ml | 31 + 32 | 5300 |
| 11. | Folic acid, $Na_2HPO_4$ | 100 ml | 33 + 34 | 5400 |
| 12. | thioctic acid, thymidine | 100 ml | 35 + 36 | 5500 |
| 13. | hypoxanthine | 100 ml | 37 | 5600 |
| 14. | rinse $H_2O$ | 2400 ml | | 8000 |
| 15. | glucose | 1000 ml | 48 | 9000 |
| 16. | rinse $H_2O$ | 1000 ml | | 10000 |
| 17. | rinse $H_2O$ | 1000 ml | | 11000 |
| 18. | NaCl | 1000 ml | 46 | 12000 |

TABLE I-continued

| | | | | | |
|---|---|---|---|---|---|
| 19. | rinse H$_2$O | 2000 ml | | | 14000 |
| 20. | glutamine | 500 ml | | 21 | 14500 |
| 21. | ZnSO$_4$ 7H$_2$O | 100 ml | | 38 | 14600 |
| 22. | Salts | 500 ml | | 39–45 | 15100 |
| 23. | rinse H$_2$O | 900 ml | | | 16000 |
| 24. | linoleic acid | 3.36 ml | | 50 | 16003.36 |
| 25. | into steel tank | | | | |
| 26. | rinse H$_2$O | 496.64 ml | | | 16500 |
| 27. | rinse H$_2$O | 500 ml | | | 17000 |
| 28. | NaHCO$_3$ | 1000 ml | | 49 | 18000 |
| 29. | phenol red | 1000 ml | | 47 | 19000 |
| 30. | rinse H$_2$O | 1000 ml | | | 20000 |

FILTER .22 MICRON

| | COMPONENTS (mg) | F-12 1 L F-12 | 1 liter Dulb 1 L Dulbecco's | 1 F-12 + Dulb 2 L (1:1) F-12 Dulbecco's | 20 liters F-12 + Dulb 20 L (1:1) F-12 Dulbecco's | VOLUME |
|---|---|---|---|---|---|---|
| AMINO ACIDS | | | | | | |
| 1. | l alanine | 8.9 | — | 8.9 | 89.0 | |
| 2. | l arginine HCl | 211.0 | 84.0 | 295.0 | 2950.0 | |
| | l arginine HCl (free base) | — | — | — | — | |
| 3. | l asparagine H$_2$O | 15.01 | — | 15.01 | 150.1 | |
| 4. | l aspartic | 13.3 | — | 13.3 | 133.0 | |
| 5. | l cysteine HCl H$_2$O | 35.12 | — | 35.12 | 351.2 | |
| 6. | l cystine 2HCl | — | — | — | — | |
| | l cystine 2HCl (crystalline) | — | 48.0 | 48.0 | 480.0 | |
| 7. | l glutamic acid | 14.7 | — | 14.7 | 147.0 | |
| 8. | glycine | 7.5 | 30.0 | 37.5 | 375.0 | |
| 9. | l histidine Hcl H$_2$O | 20.96 | 42.0 | 62.96 | 629.6 | |
| | l histidine Hcl H$_2$O (free base) | — | — | — | — | |
| 10. | l isoleucine | 3.94 | 105.0 | 108.94 | 1089.4 | |
| 11. | l leucine | 13.10 | 105.0 | 118.10 | 1181.0 | |
| 12. | l leucine HCl | 36.5 | 146.0 | 182.5 | 1825.0 | |
| 13. | l methionine | 4.48 | 30.0 | 34.48 | 344.8 | |
| 14. | l phenylalanine | 4.96 | 66.0 | 70.96 | 709.6 | |
| 15. | l proline | 34.5 | — | 34.5 | 345.0 | |
| 16. | l serine | 10.5 | 42.0 | 52.5 | 525.0 | |
| 17. | l threonin | 11.9 | 95.0 | 106.9 | 1069.0 | |
| 18. | l tyrosine | 5.4 | 72.0 | 77.4 | 774.0 | |
| | l tyrosine (disodium salt) | — | — | — | — | |
| 19. | l valine | 11.7 | 94.0 | 105.7 | 1057.0 | 2500 |
| 20. | l tryptophane | 2.04 | 16.0 | 18.04 | 180.4 | 300 |
| 21. | l glutamine | 146.0 | 584.0 | 730.0 | 7300.0 | 500 |
| 22. | sodium pyruvate | 110.0 | — | 110.0 | 1100.0 | 300 |
| VITAMINS PLUS OTHER COMPONENTS | | | | | | |
| 23. | D—Ca pantothenate, pantothenic acid, Ca salt | 0.48 | 4.0 | 4.48 | 44.8 | |
| 24. | choline chloride | 13.96 | 4.0 | 17.96 | 179.6 | |
| 25. | nicotinamide | 0.037 | 4.0 | 4.047 | 40.37 | |
| 26. | pyridoxal HCl | — | 4.0 | 4.0 | 40.62 | |
| 26a. | pyridoxine HCl | 0.062 | — | 0.062 | — | |
| 27. | thyamine HCl | 0.34 | 4.0 | 4.34 | 43.4 | |
| 28. | biotin | 0.0073 | — | 0.0073 | 0.073 | |
| 29. | i inositol | 18.0 | 7.2 | 25.2 | 252.0 | 500 |
| 30. | riboflavin | 0.038 | 0.4 | 0.438 | 4.38 | 100 |
| 31. | B 12 (cyanocobalamin) | 1.36 | — | 1.36 | 13.6 | 100 |
| 32. | putrescine 2HCl | 0.161 | — | 0.161 | 1.61 | |
| 33. | folic acid | 1.3 | 4.0 | 5.3 | 53.0 | |
| 34. | Na$_2$OHPO$_4$ | 142.04 | — | 142.04 | 1420.4 | 100 |
| 35. | lipoic acid (thioctic acid) | 0.21 | — | 0.21 | 2.1 | |
| 36. | thymidine | 0.73 | — | 0.73 | 7.3 | 100 |
| 37. | hypoxanthine Na salt | 4.77 | — | 4.77 | 47.77 | 100 |
| 38. | ZnSO$_4$ 7H$_2$O zinc sulfate | 0.863 | — | 0.863 | 8.63 | 100 |
| SALTS | | | | | | |
| 39. | FeSO$_4$ 7H$_2$O | 0.834 | — | 0.834 | 8.34 | |
| 40. | NaH$_2$PO$_4$ H$_2$O | — | 125.0 | 125.0 | 1250.0 | |
| 41. | KCl | 223.6 | 400.0 | 623.6 | 6236.0 | |
| 42. | MgCl$_2$ | 122.0 | — | 122.0 | 1220.0 | |
| 43. | MgSO$_4$ anhydrous | — | 97.67 | 97.67 | 976.7 | |
| 44. | Fe(NO$_3$)3 9H$_2$O | — | 0.1 | 0.1 | 1.0 | |
| 45. | CuSO$_4$ 5H$_2$O | 0.00249 | — | 0.0249 | 0.0249 | 500 |
| 46. | NaCl | 7599.0 | 6400.0 | 13999.0 | 139990.0 | 1000 |
| OTHER COMPONENTS | | | | | | |

TABLE I-continued

| | | | | | | |
|---|---|---|---|---|---|---|
| 47. | phenol red | 1.2 | 15.0 | 16.2 | 162.0 | 1000 |
| 48. | glucose | 1802.0 | 4500.0 | 6302.0 | 63020.0 | 1000 |
| 49. | NaHCO₃ | 1176.0 | 3700.0 | 4876.0 | 48760.0 | 1000 |
| 50. | linoleic acid albumin soln. 500 mg/20 ml | 0.084 | — | 0.084 | 0.168 | 3.36 |

Volume #1-50 = 9203.36
HCl + NaOH + H₂O rinses = 10796.64
Total Volume = 20000.00

Referring now to FIG. 1 of the drawings, a flowchart is provided which illustrates the initial culture which gave rise to the novel cell line of the present invention and the propagation of MCF-10A and MCF-10F. The symbols used in FIG. 1 are interpreted as follows: S=complete medium without serum; FF=free-floating cells transferred; T=reactivated cells; VT indicates passage by trypsin-EDTA; H =high (1.05 mM) $Ca^{++}$ with complete media; L=low (0.0, 0.03, 0.04 or 0.06 mM) $Ca^{++}$ with complete media; numbers outside the circles are days before change in media or method of passage; the circles indicate points at which cells were cryopreserved using DMSO and glycerol; the numbers within the circles are the passage of cells when reactivated; the bottom number in the circles indicates the total days of *in vitro* existence. Block A of FIG. 1 designates the initial cell cultures with alternating high or low calcium concentrations before immortalization occurred. Block B indicates MCF-10F as free-floating transfers grown in low-calcium medium. Block C represents MCF-10A as trypsin-versene passages grown in high-calcium medium.

As stated, MCF-10A and MCF-10F are substantially normal, but immortalized, human mammary epithelial cell lines as determined by the following criteria: cytogenic analysis; non-tumorigenity in nude mice; positive reactivity with milk-fat globule membrane antigens; positive reactivity with cytokeratin antiserum; three-dimensional growth in collagen; growth control by hormones and growth factors (see Table I); anchorage-dependent growth; and dome formation in confluent cultures.

With respect to the cytogenetic analysis of MCF-10A and MCF-10F, the following data were obtained as set forth in Table II below.

TABLE II

Cytogenetics:
  Chromosomes: human
  Y chromosome: absent
  Chromosome count ploidy distribution/100 metaphases:
    95 metaphases with 44 to 46 chromosomes (2N = 46)
    5 metaphases with 92+ chromosomes
  Exact chromosome count

| No. of mteaphases | 3 | 6 | 21 |
|---|---|---|---|
| No. of chromosomes: | 44 | 45 | 46 |

Figure 2:
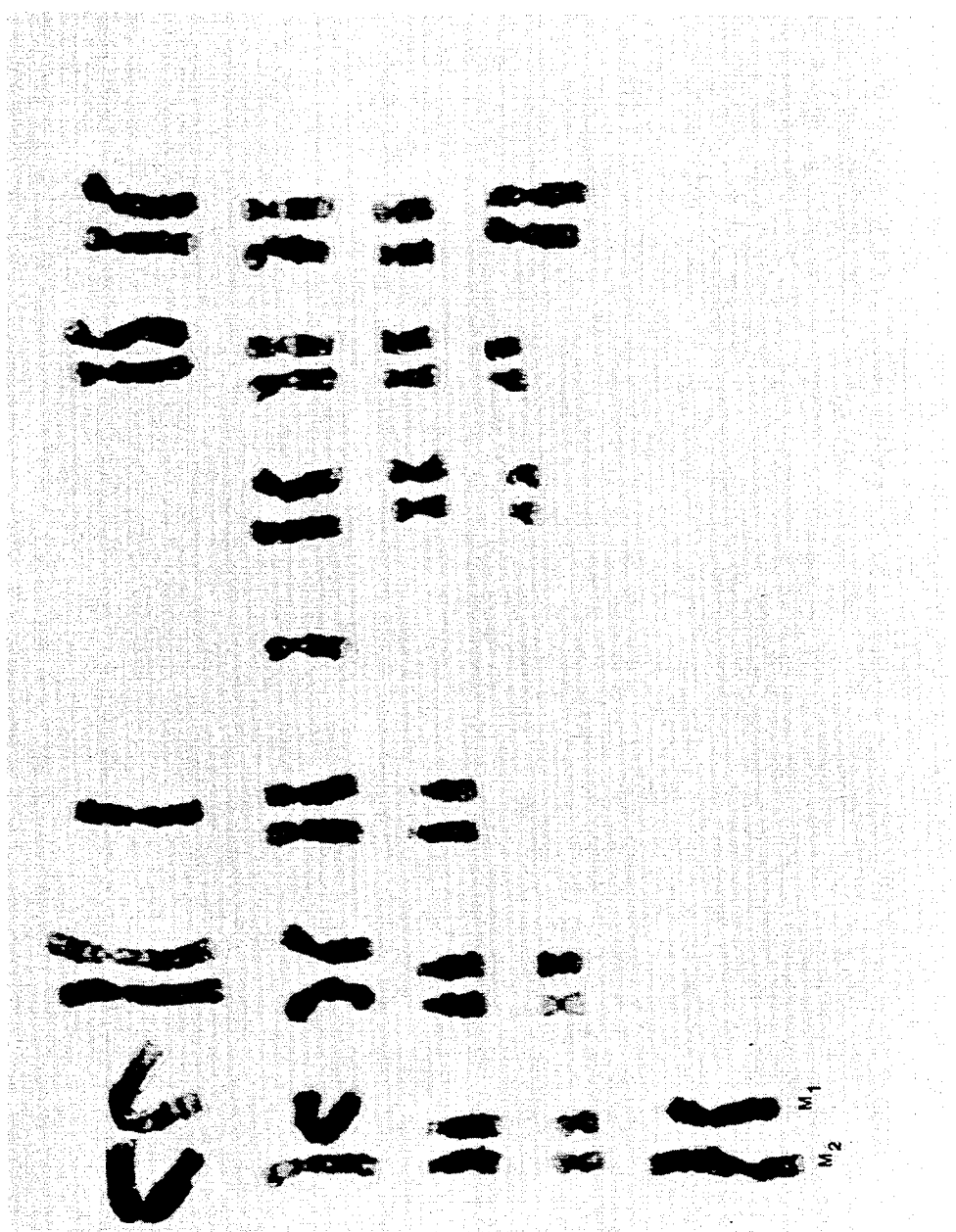
FIG. 2 is a karyotype of MCF-10F propagated free-floating transfers grown in low-calcium medium.

Giemsa banded chromosomes: Nine karyotypes were prepared from metaphases with 44 (three), 45 (two), and 46 (four) chromosomes, respectively. The karyotype for MCF-10F is shown in FIG. 2 of the drawings; the karyotypes for MCF-10A is shown in FIG. 3 of the drawings.
MCF-10 as trypsin-versene passages grown in high-calcium medium.

Normal chromosomes: All karyotypes had two X chromosomes. Normal chromosomes #3 and #9 were monosomic in all karyotypes. Chromosomes #17 and #19 were monosomic in two karyotypes each, while chromosomes #4, #10, #18, and #20 were monosomic in one karyotype each. Chromosome #18 was trisomic in one karyotype. With these exceptions, the remainder of normal chromosomes were paired.

TABLE II-continued

Marker chromosomes: Two marker chromosomes were found. Their probable origins are as follows:

M1=t(3qter>3p14::9p22>9pter)
M2=t(3pter>3p21::9q12>9q34::9p24>9qter)

Marker chromosome M2 appears to use to have the remainder of chromosomes # not found in marker M1 translocated to a chromosome #9 having a duplication of part of the q arm.

MCF-10A: 48 chromosomes; markers +8, +16, 3p−, 6p+, 9p+ (passage 105)
MCF-10F: 46 chromosomes; markers 1p+, (3:9) (passage 93)

Unassignable chromosomes: All chromosomes were assignable as either normal or as marker chromosomes.

The following further summarizes the abnormalities found in each karyotype.

| Karyotype # | Chromosome # | Monosomies | Markers | Trisomies |
|---|---|---|---|---|
| K#1 | 44 | 3,9,10,20 | M1, M2 | |
| K#2 | 44 | 3,4,9,17 | M1, M2 | |
| K#3 | 44 | 3,9,17,19 | , M2 | 18 |
| K#4 | 45 | 3,9,19 | M1, M2 | |
| M#5 | 45 | 1,9,18 | M1, M2 | |
| M#6 | 46 | 3,9 | M1, M2 | |
| M#7 | 46 | 3,9 | M1, M2 | |
| M#8 | 46 | 3,9 | M1, M2 | |
| M#9 | 46 | 3,9 | M1, M2 | |

The cell lines are aneuploid human female (XX). Most of the chromosomes are normal and paired, and most chromosome counts are at 46. However, in 8 karyotypes, chromosomes #3 and #9 are translocated as described for markers M1 and M2. The translocations are not strictly balanced, because there appears to be a duplication of the #9 q arm. A fragile site for chromosome #9 is at p22. The oncogene C-ABL is located at 9q34, which is the breakpoint for the duplication noted in marker M2. Some random loss or gain of chromosomes from metaphase to metaphase was noted from both the exact chromosome count and the karyotyping results. The following isozyme phenotypes were noted:

| LDH | G6PD | PGM1 | PGM3 | ESD | Me-2 | AK-1 | GL0-1 |
|---|---|---|---|---|---|---|---|
| human | B | 1-2 | 1 | 1 | 0 | 1 | 1-2 |

In addition to the novel cell lines of the present invention, the present invention provides a method for testing the effect of long-term exposure of epithelial cells in culture to a preselected agent. Accordingly, a culture of MCF-10A or MCF-10F would be exposed to a preselected agent, such as a suspected carcinogen. The cells would then be observed over an extended period of time to determine the effects, if any, of the exposure. In this manner, long-term studies of epithelial cells can be performed which were not previously possible.

In addition, the present invention provides a method for producing proteins from human mammary epithelial cells which comprises the steps of culturing MCF-10A or MCF-10F and collecting proteins produced by the cells. The separation and isolation of proteins from somatic cells is well known in the art and suitable methods will apparent.

The present invention has been described in connection with specific embodiments thereof; however, as will be appreciated by those skilled in the art, many modifications may be made to the invention without departing from the spirit and scope of the claims herein.

What is claimed is:

1. An immortal human mammary epithelial cell subline ATCC Registration No. CRL 10317.

2. An immortal human mammary epithelial cell subline ATCC Registration No. CRL 10318.

3. A cell culture comprising cells from a biologically pure culture of an immortal mammary epithelial cell subline ATCC Registration No. 10317.

4. A cell culture comprising cells from a biologically pure culture of an immortal mammary epithelial cell subline ATCC Registration No. 10318.

* * * * *